US006559338B1

(12) United States Patent
Bernard et al.

(10) Patent No.: US 6,559,338 B1
(45) Date of Patent: May 6, 2003

(54) METHOD FOR RACEMATE SPLITTING OF 2-HYDROXYPROPIONIC ACIDS

(75) Inventors: Harald Bernard, Wachenheim (DE); Hartmut Riechers, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/830,348

(22) PCT Filed: Oct. 16, 1999

(86) PCT No.: PCT/EP99/07858

§ 371 (c)(1),
(2), (4) Date: Apr. 25, 2001

(87) PCT Pub. No.: WO00/26170

PCT Pub. Date: May 11, 2000

(30) Foreign Application Priority Data

Oct. 30, 1998 (DE) .......................................... 198 50 301

(51) Int. Cl.[7] ................................................ C07B 57/00
(52) U.S. Cl. ....................................... 562/402; 562/401
(58) Field of Search .................................. 562/401, 402

(56) References Cited

U.S. PATENT DOCUMENTS

| 5,547,972 A | | 8/1996 | Clegg et al. | |
|---|---|---|---|---|
| 5,932,730 A | | 8/1999 | Riechers et al. | |
| 5,969,134 A | | 10/1999 | Riechers et al. | |
| 6,030,975 A | * | 2/2000 | Romerdahl | ................. 514/274 |

* cited by examiner

*Primary Examiner*—Paul J. Killos
(74) *Attorney, Agent, or Firm*—Wood, Phillips, Katz, Clark & Mortimer

(57) ABSTRACT

A process for racemate resolution of 2-hydroxypropionic acids by reacting the racemic acid with an optically active base and subsequently separating off a diastereomeric salt of acid and base comprises using 1-(4-chlorophenyl) ethylamine as optically active base.

6 Claims, No Drawings

METHOD FOR RACEMATE SPLITTING OF 2-HYDROXYPROPIONIC ACIDS

The present invention relates to a process for the racemate resolution of 2-hydroxypropionic acids by reacting the racemic acid with an optically active base and subsequently separating off a diastereomeric salt of acid and base. 2-hydroxypropionic acids are important intermediates for the synthesis of plant protection agents and pharmaceuticals. Since the action of such substances is frequently due to only one enantiomer, it is desirable to prepare these active ingredients in high optical purity. It is therefore advisable to plan the synthesis in such a manner that racemic intermediates can be separated into their enantiomers in order subsequently to obtain enantiomerically pure end products.

BACKGROUND OF INVENTION

WO 93/13075, which is equivalent to U.S. Pat. No. 5,547,972, describes propionic acids 2-substituted by heterocycles as potent endothelin-receptor antagonists for treating cardiovascular disorders. These active ingredients are synthesized using 2-hydroxypropionic acids as intermediates.

WO 96/11914 describes the preparation on a laboratory scale of (S)-2-hydroxy-3-methoxy-3,3-diphenylpropionic acid by racemate resolution using L-proline methyl ester (Example 10) and (S)-1-(4-nitrophenyl)ethylamine (Example 11). In this manner a yield of 35% based on the racemate and an optical purity of 99.8% are achieved.

BRIEF DESCRIPTION OF INVENTION

However, it has been found that when this described reaction step was scaled up (several kg to 100 kg), additional working steps became necessary in order to ensure a high optical purity. The diastereomeric salt of (S)-2-hydroxypropionic acid and (S)-1-(4-nitrophenyl)ethylamine crystallizes with difficulty and can therefore not be filtered off readily, either, so that some of the mother liquor remains in the crystals together with the enantiomer to be separated off. Only when the crystals were additionally stirred in the tank together with fresh solvent, and when the crystals which had been filtered off once more had been copiously rewashed, was the required optical purity obtained.

It is an object of the present invention, therefore, to provide a process for racemate resolution which does not have the abovementioned disadvantages but can readily be carried out on an industrial scale.

We have found that this object is achieved by a process for racemate resolution of 2-hydroxypropionic acids by reacting the racemic acid with an optically active base and subsequently separating off a diastereomeric salt of acid and base, which comprises using 1-(4-chlorophenyl)ethylamine as optically active base.

DETAILED DESCRIPTION OF INVENTION

The preparation of 2-hydroxypropionic acids is familiar to those skilled in the art from organic synthesis manuals as described, for example, in WO 96/11914.

The process according to the invention is particularly suitable for the racemate resolution of 2-hydroxypropionic acids which are monosubstituted or polysubstituted at the 3 position, in particular 2-hydroxypropionic acids which, at the 3 position, bear from one to two aryl radicals, preferably phenyl.

A particularly preferred embodiment of the process according to the invention is the racemate resolution of 2-hydroxy-3-methoxy-3,3-diphenylpropionic acid and 2-hydroxy-3-methyl-3,3-diphenylpropionic acid.

The process according to the invention is usually carried out in such a manner that a solution of xmol of the racemic 2-hydroxypropionic acid, if necessary with heating, is admixed with about 0.5–0.6xmol of optically active 1-(4-chlorophenyl)ethylamine and then one of the diastereomeric salts formed is separated off.

In a preferred embodiment, seed crystals of the diastereomeric salt to be separated off are added to the solution and the solution is allowed to cool slowly, which produces a good crystallization. The seed crystals can be added after all of the optically active base has been added or even earlier, if only a portion, preferably about half, of the required base has been added.

If the other enantiomer of the 2-hydroxypropionic acid is wanted, this can also then be isolated from the mother liquor.

A preferred solvent for the racemate separation is a mixture of alcohol and ether, in particular of methanol and methyl tert-butyl ether (MTB). An alcohol, in particular isopropanol, is preferably used for the racemate resolution of 3-hydroxy-3-methyl-3,3-diphenylpropionic acid.

The process according to the invention has the advantages that it produces enantiomerically pure 2-hydroxypropionic acid in a very good yield and can be scaled up to the industrial level without problems. The crystals of the diasteromeric salt of 2-hydroxypropionic acid and 1-(4-chlorophenyl)ethylamine settle surprisingly well in the mother liquor and can therefore be separated off by filtration without problems. Complex rewashing of the crystals to achieve the desired enantiomeric purity is not necessary. This is a substantial advantage in comparison with the diastereomeric salt of 2-hydroxypropionic acid and 1-(4-nitrophenyl)ethylamine. Thus, complex transfer operations, stirring steps and rewashing steps can be saved, which decreases energy consumption and the amount of solvent, and the space-time yield of a given plant can be substantially increased.

The example below illustrates the process according to the invention on an industrial scale.

EXAMPLE 1

Preparation of (S)-p-chlorophenylethylammonium (S)-2-hydroxy-3-methoxy-3,3-diphenylpropionate by racemate resolution A solution of 129.0 kg (474 mol) of 2-hydroxy-3-methoxy-3,3-diphenylpropionic acid in 650 l of MTB and 650 l of methanol is heated to 55° C. and, with agitation and maintenance of the solution at 55° C., 37.0 kg (237 mol) of (S)-p-chlorophenylethylamine are added. After addition of half of the amount of amine, seeding with (S)-p-chlorophenylethylammonium (S)-2-hydroxy-3-methoxy-3,3-diphenylpropionate is performed, with crystallization starting. When all of the amine has been added, the mixture is further stirred for one hour at 55° C. and then cooled to 3° C. at a cooling rate of 10° C. per hour.

The resulting suspension is filtered off on a single-layer filter and rewashed with 300 l of MTB cooled to 3° C. The product is dried on the filter in a nitrogen stream, with the jacket heated to 40° C.

Yield: 73.9 kg (172.7 mol) equivalent to 36.4% of theory (based on racemate)

HPLC: 99.8%

Chiral HPLC: >99.95%

EXAMPLE 2

A solution of 35.5 kg (134.4 mol) of 2-hydroxy-3-methyl-3,3-diphenylpropionic acid in 155 kg of isopropanol is heated for 2 h at from 75 to 80° C. and 13.75 kg of 1-(4-chlorophenyl)ethylamine are added. After addition of seed crystals, the mixture is refluxed for a further 2 h and cooled to room temperature at steps of 5° C./h. The resultant suspension is filtered off with suction via a single-layer filter and washed twice with 12 kg of cooled isopropanol. The product is dried in the filter in a nitrogen stream, with the jacket heated to 40° C. If necessary, the product is recrystallized from isopropanol (isopropanol amount [L]=mass of the wrong enantiomer [kg]/0.027 kg/L).

Yield: 21.1 kg (517.2 mol), purity: 99.2% equivalent to 38% based on racemate, ee=94%

We claim:

1. The process for the racemates resolution of a 2-hydroxypropionic acid which comprises reacting the racemic acid with an optically active base and subsequently separating off a diastereomeric salt of acid and base, wherein the optically active base is 1-(4-chlorophenyl)ethyl amine.

2. The process of claim 1 wherein the racemic acid is 2-hydroxy-3-methoxy-3,3-diphenylpropionic acid.

3. The process of claim 1 wherein the racemic acid is 2-hydroxy-3-methyl-3,3-diphenylpropionic acid.

4. The process of claim 1 wherein the optically active base is (S)-1-(4-chlorophenyl)ethyl amine.

5. The process of claim 2 wherein the reaction is carried out in a solvent, which comprises a mixture of methanol and methyl tert-butyl ether.

6. The process of claim 3 wherein the reaction is carried out in a solvent, which comprises isopropanol.

* * * * *